US009572940B2

(12) United States Patent
Horlock (10) Patent No.: US 9,572,940 B2
(45) Date of Patent: Feb. 21, 2017

(54) DRIVE ASSEMBLY FOR A MEDICATION DELIVERY DEVICE AND MEDICATION DELIVERY DEVICE

(75) Inventor: Mark Philip Horlock, Timperley (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1087 days.

(21) Appl. No.: 13/701,957

(22) PCT Filed: Jun. 9, 2011

(86) PCT No.: PCT/EP2011/059563
§ 371 (c)(1),
(2), (4) Date: Apr. 9, 2013

(87) PCT Pub. No.: WO2011/154480
PCT Pub. Date: Dec. 15, 2011

(65) Prior Publication Data
US 2013/0204205 A1  Aug. 8, 2013

(30) Foreign Application Priority Data
Jun. 11, 2010 (EP) .................................... 10165636

(51) Int. Cl.
*A61M 5/315* (2006.01)
*A61M 5/31* (2006.01)

(52) U.S. Cl.
CPC ..... *A61M 5/31501* (2013.01); *A61M 5/31543* (2013.01); *A61M 5/31555* (2013.01);
(Continued)

(58) Field of Classification Search
CPC ..................... A61M 5/31501; A61M 5/31543; A61M 5/31555; A61M 5/31585; A61M 2005/3151
See application file for complete search history.

(56) References Cited

U.S. PATENT DOCUMENTS 1,718,596 A   6/1929  Smith
4,592,745 A   6/1986  Rex et al.
(Continued)

FOREIGN PATENT DOCUMENTS

JP   H07-500039   1/1995
JP   H08-00730    1/1996
(Continued)

OTHER PUBLICATIONS

English Translation of the Notice of Reason for Rejection issued in Japanese Patent Application No. 2013-513686 dated Mar. 3, 2015.
(Continued)

*Primary Examiner* — Laura Bouchelle
*Assistant Examiner* — Anh Bui
(74) *Attorney, Agent, or Firm* — McDonnell Boehnen Hulbert & Berghoff LLP (57) ABSTRACT

A drive assembly for a medication delivery device is provided which is switchable from an operational state to a resetting state and which comprises:
  a housing having a proximal end and a distal end,
  a drive member adapted to be rotated with respect to the housing, and
  a stop member adapted to prevent rotational movement of the drive member in a first direction with respect to the housing and to permit rotational movement of the drive member in a second direction with respect to the housing, the second direction being opposite to the first direction. In the operational state of the drive assembly the stop member is held in engagement with the drive member, and for switching into the resetting state of the drive assembly the stop member is enabled to disengage from the drive member caused by gravity due to the weight of the stop member. Moreover, in the operational state of the drive assembly the drive mem-
(Continued)

ber may be held in engagement with a rotation member, and for switching into the resetting state of the drive assembly the drive member may be enabled to disengage from the rotation member caused by gravity due to the weight of the drive member.

20 Claims, 7 Drawing Sheets

(52) U.S. Cl.
CPC ..... *A61M 5/31585* (2013.01); *A61M 5/31568* (2013.01); *A61M 2005/3125* (2013.01); *A61M 2005/3151* (2013.01)

(56) References Cited

U.S. PATENT DOCUMENTS

| | | | |
|---|---|---|---|
| 5,725,508 | A | 3/1998 | Chanoch et al. |
| 2004/0210199 | A1* | 10/2004 | Atterbury ......... A61M 5/31566 604/224 |
| 2009/0275914 | A1* | 11/2009 | Harms ................. A61M 5/24 604/506 |

FOREIGN PATENT DOCUMENTS

| | | |
|---|---|---|
| WO | 9307922 A1 | 4/1993 |
| WO | 93/14799 | 8/1993 |
| WO | 2007/099044 | 9/2007 |

OTHER PUBLICATIONS

International Search Report for Int. App. No. PCT/EP2011/059563, completed Dec. 15, 2011.
Form PCT/ISA/220; Notification of Transmittal of the International Search Report and the Written Opinion of the International Searching Authority, or the Declaration dated Dec. 23, 2011.
Form PCT/IB/326; Notification Concerning Transmittal International Preliminary Report on Patentability dated Dec. 27, 2012.
English Translation of the Notice of Reason for Rejection Issued in Japanese Pateent Application No. 2013-513686 dated Mar. 3, 2015.

* cited by examiner

DRIVE ASSEMBLY FOR A MEDICATION DELIVERY DEVICE AND MEDICATION DELIVERY DEVICE

CROSS REFERENCE TO RELATED APPLICATIONS

The present application is a U.S. National Phase Application pursuant to 35 U.S.C. §371 of International Application No. PCT/EP2011/059563 filed Jun. 9, 2011, which claims priority to European Patent Application No. 10165636.1 filed Jun. 11, 2010. The entire disclosure contents of these applications are herewith incorporated by reference into the present application.

FIELD OF INVENTION

The present invention relates to a drive assembly for a medication delivery device and a corresponding medication delivery device for delivering a dose of a medication, wherein the medication delivery device is for example a reusable pen-type injection device. The device may be configured to dispense variable doses of the medication where a user can vary the size of a dose. Alternatively, the device may be a fixed dose device, in particular a device configured to dispense doses of the drug which may not be varied by the user. The drug delivery device may be a manually, in particular a non-electrically driven device.

BACKGROUND

In particular, the present invention may relate to such medication delivery devices where a user may set a dose of medication to be delivered from a multi-dose cartridge. Most preferably, the medication delivery device comprises a single- or multi-dose medication cartridge which can be replaced when the medication for example has been fully dispensed or has passed its date of expiry.

Medication delivery devices of the kind mentioned above have become widespread where regular injections by persons without formal medical training occur. This is increasingly common among those having diabetes where self-treatment enables such persons to conduct effective management of their diabetes.

As a result of environmental and economical reasons, medication delivery devices of the type mentioned above have been developed to allow only a part of the device to be discarded, usually the medication cartridge only, and the other part to be reused. This provides the additional requirement for such a medication delivery device that a resetting of the drive assembly, when a new cartridge is attached to or inserted into the medication delivery device, has to be enabled and needs to be easy and unambiguous, thereby reducing the possibility of damage to the drive assembly.

SUMMARY

It is an object of the present invention to disclose a drive assembly for a medication delivery device as well as a medication delivery device which facilitate their resetting and which nevertheless are cost-effective.

In a first aspect, this object is achieved with the drive assembly for a medication delivery device according to claim 1.

The drive assembly is switchable from an operational state to a resetting state and comprises:

a housing having a proximal end and a distal end,
a drive member adapted to be rotated with respect to the housing, and
a stop member adapted to prevent rotational movement of the drive member in a first direction with respect to the housing and to permit rotational movement of the drive member in a second direction with respect to the housing, the second direction being opposite to the first direction, wherein
in the operational state of the drive assembly the stop member is held in engagement with the drive member, and
for switching into the resetting state of the drive assembly the stop member is enabled to disengage from the drive member caused by gravity due to the weight of the stop member.

In this concept of a drive assembly for a medication delivery device the stop member and the drive member are engaged with each other during the operational state, the drive member having driving functionality in the drive assembly for medication delivery purposes. As an example, the drive member may act on a piston rod, thereby causing a movement of the piston rod in distal direction for delivery a dose of medication. The drive assembly may provide for a simple and effective separation of the stop member and the drive member under gravity. A disengagement of stop member and drive member can thus be obtained such that the drive assembly becomes resettable. Preferably, the drive member becomes freely rotatable relative to the stop member, in particular in the first direction with respect to the housing. This may provide for a simple reset action of the drive assembly and may aid all users, but particularly those with impaired dexterity, for resetting the drive assembly. As the disengagement of the drive member and the stop member is realized under gravity, no further elements may be necessary for separating the two members. Hence, the device may be cost-effective.

The term "operational state" according to the present invention shall preferably mean a state of the drive assembly, where a dispensing of medication is enabled. Moreover, it preferably means a state in which the drive member is enabled to drive at least one element of a medication delivery device, for example a piston rod, such that medication can be delivered. For this purpose, stop member and drive member may be held in engagement with each other such that the drive member is restricted to rotational movement in a single direction, i.e. the second direction, for predetermined driving of the drive assembly.

The term "resetting state" according to the present invention shall preferably mean a state of the drive assembly, where a resetting of the drive assembly is enabled. Resetting shall preferably mean an action of bringing at least one element, which has been moved in the operational state, back into an initial position for enabling reuse of the assembly in a following operational state, preferably after changing a medication cartridge. For this purpose, the stop member may be enabled to disengage from the drive member such that the movement of the drive member is no longer restricted to a single direction, i.e. the second direction, and the drive member may be enabled to move in the first and in the second direction with respect to the housing. A movement of the drive member in the first direction may mean a resetting movement which preferably is opposed to the movement for delivering a medication. Hence, the drive assembly may be reset by the drive member rotationally moving in the first direction in an opposed manner as the drive member moves in the operational state for driving at least one element of the medication delivery device.

The term "distal end" according to the present invention shall mean the end of the drive assembly or a component of the drive assembly which is closest to a dispensing end of a medication delivery device in which the drive assembly is incorporated.

The term "proximal end" according to the present invention shall mean the end of the drive assembly or a component of the drive assembly which is furthest away from a dispensing end of a medication delivery device in which the drive assembly is incorporated. Preferably a button or other dosing element is provided at the proximal end of the drive assembly which may be pushed for dose delivery.

The term "housing" shall preferably mean any exterior housing ("main housing", "body", "shell") or interior housing ("insert", "inner body"). The housing may be designed to enable the safe, correct, and comfortable handling of the medication delivery device or any of its mechanism.

The term "medication", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound.

In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Turning now again to the design of the drive assembly, in a preferred embodiment the drive assembly comprises a rotation member adapted to be rotated in the first direction with respect to the housing during setting of a dose of a medication and to be rotated in the second direction with respect to the housing during delivery of the dose. The rotation member may fulfil two functionalities during the operational state. A first functionality may comprise rotational movement of the rotation member for setting a predetermined dose of a medication. A second functionality may comprise rotational movement of the rotation member in an opposite direction for delivery of a medication.

Preferably the rotation member is arranged at an opposite side of the drive member with respect to the stop member. That means, the drive member is arranged between the stop member on one side and the rotation member on the other side. According to this arrangement, the drive member can interact with the stop member on one side, and can interact with the rotation member on the other side.

In a preferred embodiment the drive assembly is provided such that in the operational state of the drive assembly the drive member is held in engagement with the rotation member. Thus, the rotation member can interact with the drive member thereby transmitting its rotational movement to the drive member, preferably for delivery of a preset dose of a medication. Preferably, for switching into the resetting state of the drive assembly, the drive member is enabled to be disengaged from the rotation member caused by gravity due to the weight of the drive member. The drive assembly may provide for a simple and effective separation of the drive member and the rotation member under gravity. A disengagement of drive member and rotation member can thus be obtained. In one embodiment resetting of the drive assembly may be enabled by a free rotation of the drive member relative to the rotation member. Thus rotational movement of the drive member in the first direction according to a resetting state of the drive assembly may not effect any rotational movement of the rotation member. Preferably, in the resetting state of the drive assembly the drive member interacts neither with the stop member nor with the rotation member due to the respective gravity separation and is enabled to freely rotate relative to the stop member and relative to the rotation member.

In a preferred embodiment the drive assembly comprises a resilient member. The term "resilient member" as used herein shall preferably mean any resilient element that is provided for exerting a force on a component and/or components, for example to ensure that these components are forced together, e.g. into engagement, or forced apart, e.g. out of engagement. Preferably the resilient member may be manufactured from any suitable flexible energy storage material known by a person skilled in the art, e.g. metal, rubber or plastics, and may take any suitable form, e.g. a spring.

Preferably, the resilient member is adapted to provide a force for engagement of the stop member and the drive member. This means that the resilient member may push the stop member in a direction towards the drive member such that stop member and drive member may be held in engagement, preferably in direct abutment.

Furthermore, the resilient member is preferably adapted to provide a force for engagement of the drive member and the rotation member in the operational state. This means that the resilient member may push the drive member in a direction towards the rotation member such that drive member and rotation member are held in engagement, preferably in direct abutment. It follows that in the operational state the resilient member preferably keeps the stop member and the drive member as well as the stop member and the rotation member in engagement such that the respective elements may directly interact with each other.

In a preferred embodiment the resilient member is adapted to interact with a medication receptacle of a medication delivery device. The term "medication receptacle" in this context shall preferably mean a cartridge containing a medication or a cartridge assembly, most preferably a cartridge holder for receiving a cartridge containing a medication. When such a medication receptacle is engaged with the housing the resilient member may be strained, thereby providing the corresponding force for holding the elements in engagement. When a respective medication receptacle is disengaged from the housing the resilient member may be unstrained, thereby not providing the corresponding force for holding the elements in engagement. That means, the drive assembly preferably is in the operational state when the medication receptacle is engaged with the housing and in the resetting state when the medication receptacle is disengaged from the housing. Gravity separation in the resetting state may be obtained by disengaging and removing the medication receptacle from the housing and bringing the drive assembly in a predetermined position with the distal end of the drive assembly pointing downwards. Switching of the drive assembly between the two states may preferably be achieved by engaging or disengaging the medication receptacle with or from the housing.

Preferably the drive assembly is designed such that in the operational state the drive member is adapted to follow rotational movement of the rotation member in the second direction with respect to the housing during delivery of the dose. Preferably, the drive member and the rotation member are coupled to one another by a first uni-directional friction clutch mechanism, which is configured to permit relative rotational movement between rotation member and drive member during rotation of the rotation member in the first direction for setting of the dose and to prevent relative rotational movement of rotation member and drive member during rotation of the rotation member in the second direction for delivery of the dose. By use of the first uni-directional friction clutch mechanism the rotation member may slide along the drive member in the first direction without transmitting its rotational movement to the drive member, whereas the rotation member may come into engagement with the drive member in the second direction, thereby transmitting its rotational movement to the drive member. According to this mechanism, the drive member may only be urged to follow rotational movement of the rotation member in the second direction with respect to the housing and to fulfil driving functionality for delivering the predetermined dose of the medication.

Preferably the drive assembly comprises a dose member which is movable with respect to the housing and wherein movement of the dose member with respect to the housing is converted into rotational movement of the rotation member with respect to the housing. The dose member is preferably arranged such that a user may grip and move it for setting a predetermined dose of a medication. During movement of the dose member the rotation member may rotationally be moved, preferably in the first direction, for setting the respective dose as the rotation member may directly or indirectly be coupled with the dose member. The movement of the dose member can be any kind of movement, e.g. an axial movement or rotational movement or a combination thereof.

In a preferred embodiment the drive assembly is designed such that in the operational state the stop member and the drive member are coupled to one another by a second uni-directional friction clutch mechanism, which is configured to prevent relative rotational movement between stop member and drive member in the first direction with respect to the housing and to permit relative rotational movement of stop member and drive member in the second direction with respect to the housing. This second uni-directional friction clutch mechanism may inhibit any movement of the drive member in the first direction during setting of a dose. Rotational movement of the drive member for driving the drive assembly may be only possible in the second direction as the drive member follows rotational movement of the rotation member in the second direction and may slide along the stop member without being inhibited in its rotational movement in the second direction for delivering the preset dose of the medication.

Preferably in the resetting state the stop member or both the stop member and the drive member are adapted to be movable in the distal direction with respect to the housing caused by gravity when the drive assembly is positioned in the predetermined position with its distal end pointing downwards. Preferably, the traverse path of the respective members in distal direction with respect to the housing is delimited by mechanical stopping means. When the stop member and the drive member and/or the drive member and the rotation member become separated under gravity during switching into the resetting state, the stop member or both the stop member and the drive member may be moved away from the rotation member. Preferably, the rotation member is axially fixed with respect to the housing. The stop member or both the stop member and the drive member may be enabled to be brought from respective first positions taken up during the operational state into respective second positions taken up during the resetting state during gravity separation. For preventing a movement of the stop member and the drive member beyond their respective second position after the gravity separation, mechanical stopping means may be provided. Due to the stopping means, the stop member and the drive member may be undetachably connected to the housing of the drive assembly.

Preferably the traverse path of the stop member is longer than the traverse path of the drive member. That means that for a complete gravity separation of the elements the stop member may have to move along a traverse path which is longer than the traverse path of the drive member.

In a preferred embodiment the drive assembly comprises a piston rod adapted to be displaced in the distal direction with respect to the housing for delivery a dose of a medication.

The term "piston rod" as used herein shall preferably mean a component adapted to operate through/within the housing and designed to be moveable in axial direction (preferably towards the distal end) through/within the medication delivery device and to translate its axial movement preferably to a piston or bung of the cartridge for the purpose of discharging/dispensing a medication from the cartridge. Said piston rod may be flexible or not. It may be a simple rod, a lead-screw, a part of a rack and pinion system, a part of a worm gear system or the like. The piston rod shall further mean a component having a circular or a non-circular cross-section. It may be made of any suitable material known by a person skilled in the art.

Preferably, in the operational state of the drive assembly rotational movement of the drive member in the second direction with respect to the housing is converted into a movement of the piston rod in the distal direction with respect to the housing. According to this mechanism, in the operational state the drive member drives the piston rod in the distal direction such that a dose of a medication can be expelled out of a cartridge of a medication delivery device in which the drive assembly may be incorporated. In the resetting state of the drive assembly rotational movement of the piston rod in the proximal direction with respect to the housing may be converted into rotational movement of the drive member in the first direction with respect to the housing. The drive member can, e.g. directly be engaged with the piston rod, especially via a splined connection. But it is also conceivable that the drive member is indirectly engaged with the piston rod via another element connecting the drive member to the piston rod.

In a second aspect the object of the present invention is achieved with a medication delivery device, wherein the medication delivery device comprises the drive assembly of the preceding type and a medication receptacle being removable from a housing of the drive assembly. The medication receptacle is preferably of the type as described above and configured for containing at least one dose of a medication. The drive assembly preferably comprises a drive member and a piston rod, the drive member cooperating with the piston rod for axially displacing the piston rod, preferably in a distal direction with respect to the housing of the drive assembly, for delivering a dose of a medication. Preferably, the device is switchable from an operational state into a resetting state by removing the medication receptacle from the housing of the drive assembly, by bringing the device into a predetermined position, and by subsequent gravity separation of drive assembly members. Preferably the predetermined position is a vertical position of the device with the distal end of the piston rod pointing downwards. In the resetting state the piston rod is movable in a proximal direction into the housing of the drive assembly.

According to this concept, the medication delivery device comprises a drive assembly of the type described above for setting and delivering a dose of a medication, wherein the drive member drives the piston rod in a distal direction for delivering the dose. The device can be held in the predetermined position such that after removing the medication receptacle from the housing of the drive assembly the drive member or the drive member and the stop member are moved downwards along a predetermined traverse path. Hence, the stop member and the drive member as well as the drive member and the rotation member may be separated, caused by gravity. Thereby, the drive member is preferably disengaged from the rotation member. The stop member is preferably disengaged from the drive member. This may enable the drive member to freely rotate in a first direction without being inhibited by the stop member and/or the rotation member such that the piston rod, which is pointing downwards in the position as mentioned above, can be pushed upwards in a proximal direction of the device and back into the housing of the drive assembly for resetting the medication delivery device.

During movement of the piston rod in this proximal direction, the drive member may freely rotate. After the resetting has been accomplished, a new medication receptacle with a new cartridge of a medication may be enabled to be inserted or attached to the housing of the drive assembly. The medication delivery device thus can be brought into the operational state again.

This concept of a medication delivery device may provide for a simple reset action and may aid all users, but particularly those with impaired dexterity, to reset the device. As the device uses the drive assembly of the type mentioned above, the device may be cost-effective.

Further features, refinements and expediencies become apparent from the following description of the exemplary embodiments in connection with the figures.

DETAILED DESCRIPTION

Figure 1:
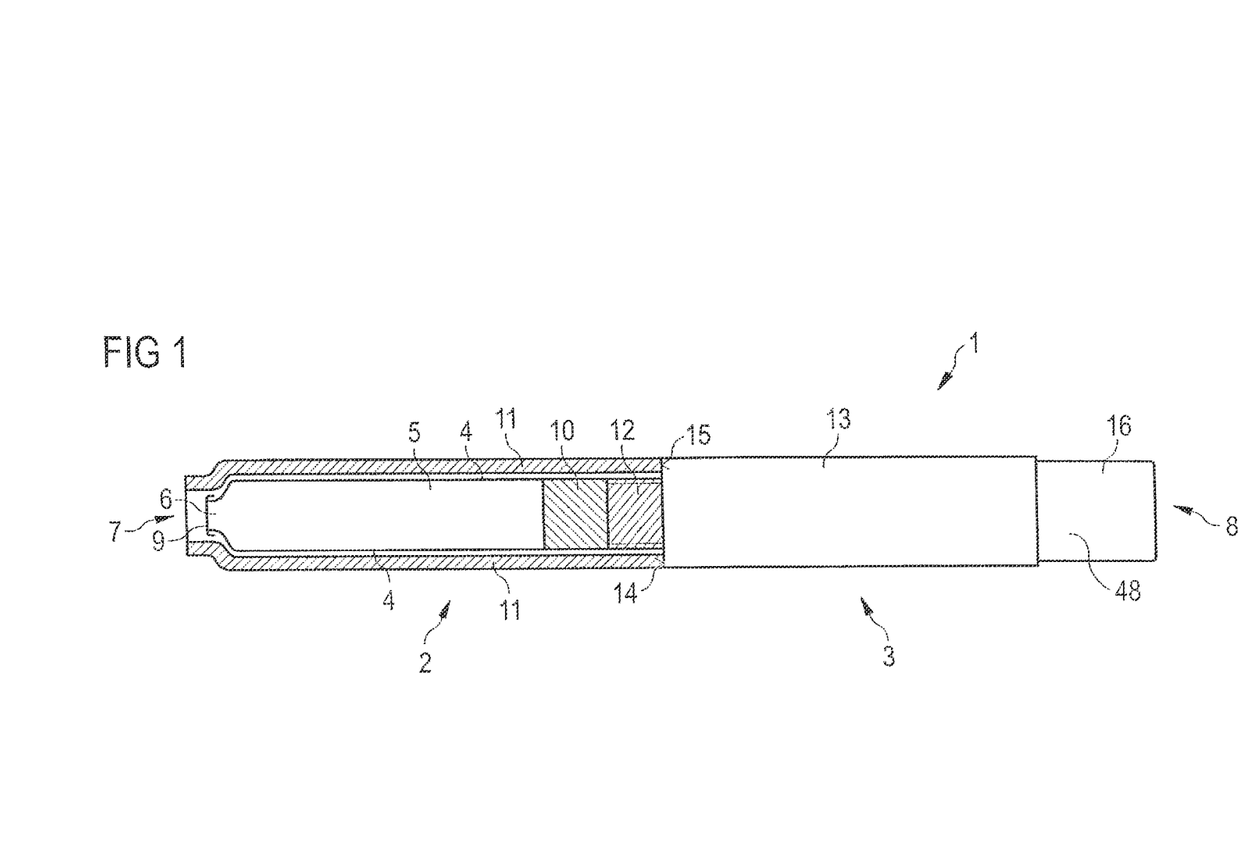
FIG. 1 schematically shows a partly sectional side view of an exemplary embodiment of a medication delivery device.

Turning now to FIG. 1, a medication delivery device 1 comprises a medication receptacle 2 and a drive assembly 3. The medication receptacle 2 comprises a cartridge 4. Medication 5 is retained in the cartridge 4. The medication 5 is preferably liquid medication. The cartridge 4 preferably comprises a plurality of doses of the medication 5. The medication 5 may comprise for example insulin, heparin, growth hormones or any other composition of the type named above. The cartridge 4 has an outlet 6 at its distal end. Medication 5 can be dispensed from the cartridge through outlet 6. The device 1 may be a pen-type device, in particular a pen-type injector. The device 1 may be a disposable or a reusable device. The device 1 may be a device configured to dispense fixed doses of the medication or variable, preferably user-settable, doses. The device 1 may be a needle-based or a needle free device. The device 1 may be an injection device.

In FIG. 1, the distal end of the device 1 was assigned reference numeral 7 and the proximal end of the device was assigned reference numeral 8.

The outlet 6 may be covered by a membrane 9, which protects medication 5 against external influences during storage of the cartridge. For medication delivery, membrane 9 may be opened, e.g. pierced. For example, membrane 9 may be pierced by a needle unit (not explicitly shown). The needle unit may be (releasably) attached to the distal end of the medication receptacle 2. The needle unit may provide for fluid communication from the inside of the cartridge 4 to the outside of the cartridge through outlet 6.

A piston 10 is retained within the cartridge 4. The piston 10 is movable with respect to the cartridge. The piston 10 may seal the medication 5 within the cartridge. The piston 10 expediently seals the interior of the cartridge 4 proximally. Movement of the piston 10 with respect to the cartridge 4 in the distal direction causes medication 5 to be dispensed from the cartridge through outlet 6 during operation of the device.

The medication receptacle 2 furthermore comprises a cartridge retaining member 11. The cartridge 4 is retained within the cartridge retaining member 11. The cartridge retaining member 11 may stabilize the cartridge 4 mechanically. Additionally or alternatively, the cartridge retaining member 11 may be provided with a fixing member (not explicitly shown) for attaching the medication receptacle 2 to the drive assembly 3.

The medication receptacle 2 and the drive assembly 3 are secured to one another, preferably releasably secured. A medication receptacle 2 which is releasably secured to the drive assembly may be detached from the drive assembly 3, for example in order to allow for providing for a new cartridge 4, if all of the doses of medication which once were in the cartridge formerly attached to the drive assembly 3 have already been dispensed. The cartridge retaining member 11 may be releasably secured to the drive assembly 3 via a thread, for example.

Alternatively, the cartridge retaining member 11 may be dispensed with. It is particularly expedient, in this case, to apply a robust cartridge 4 and to attach the cartridge directly to the drive assembly 3.

The drive assembly 3 is configured for transferring force, preferably user-exerted force, particularly preferably manually exerted force, to the piston 10 for displacing the piston 10 with respect to the cartridge 4 in the distal direction. A dose of medication may be dispensed from the cartridge in this way. The size of the delivered dose may be determined by the distance by which the piston 10 is displaced with respect to the cartridge 4 in the distal direction.

Furthermore, the drive assembly comprises a piston rod 12. The piston rod 12 may be configured for transferring force to the piston 10, thereby displacing the piston 10 in the distal direction with respect to the cartridge 4. A distal end face of the piston rod 12 may be arranged to abut a proximal end face of the piston 10. A bearing member (not explicitly shown) may be arranged to advance the piston 10, preferably to abut the proximal end face of the piston 10. The bearing member may be arranged between piston 10 and piston rod 12. The bearing member may be fixed to the piston rod 12 or a separate member. If the piston rod 12 is configured to be rotated during operation of the device, for example during dose delivery, it is particularly expedient to provide for a bearing member. The bearing member may be displaced together with the (rotating) piston rod 12 with respect to the housing. The piston rod 12 may be rotatable with respect to the bearing member. In this way, the risk that the rotating piston rod 12 drills into the piston and thereby damages the piston is reduced. Accordingly, while the piston rod 12 rotates and is displaced with respect to the housing, the bearing member is preferably only displaced, i.e. does not rotate. The piston rod 12 may be bounded by the bearing member.

The drive assembly 3 comprises a housing 13 which the piston rod 12 may be retained in. A proximal end side 14 of the medication receptacle 2 may be secured to the drive assembly 3 at a distal end side 15 of the housing 13, for example via a threaded connection. Housing 13, cartridge 4 and/or cartridge retaining member 11 may have a tubular shape.

The drive assembly 3 comprises a dose part 16. The dose part 16 is movable with respect to the housing 13. The dose part 16 may be movable in the proximal direction with respect to the housing for setting of a dose of the medication 5 which is to be delivered and in the distal direction with respect to the housing for delivery of the set dose. The dose part 16 is preferably connected to the housing 13. The dose part 16 may be secured against rotational movement with respect to the housing. The dose part 16 may be moved (displaced) between a proximal end position and a distal end position with respect to the housing 13 (not explicitly shown). The distance by which the dose part is displaced with respect to the housing during setting of the dose may determine a size of the dose. The proximal end position and the distal end position may be determined by a respective stop feature which may limit the proximal or distal travel of the dose member with respect to the housing. The device 1 may be a variable dose device, i.e. a device configured for delivering doses of medication of different, preferably user-settable, sizes. Alternatively, the device may be a fixed dose device.

The device 1 may be a manually, in particular non-electrically, driven device. The (user-applied) force which causes the dose part 16 to be moved with respect to the housing 13 in the distal direction may be transferred to the piston rod 12 by the drive assembly 3. For this purpose, drive assembly members may be provided which are not explicitly shown in FIG. 1. The drive assembly 3 is preferably configured to not move the piston rod 12 with respect to the housing 13 when the dose part is moved in the proximal direction with respect to the housing for setting of the dose.

An embodiment of a drive assembly which is suitable for being implemented in the medication delivery device 1 as described above is described in connection with FIGS. 2 and 3.

Figure 2:
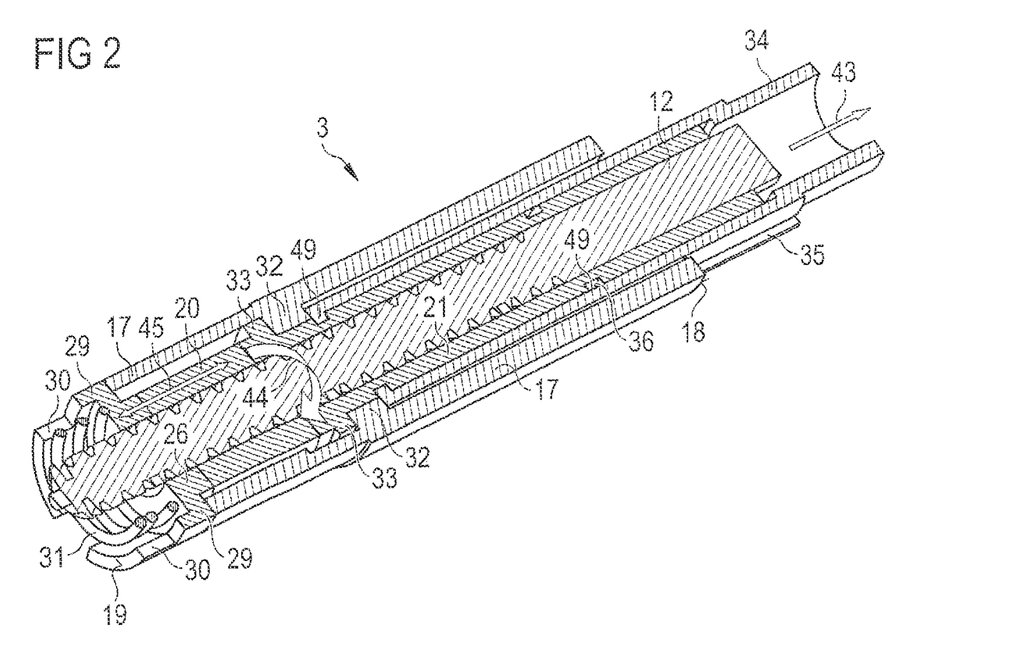
FIG. 2 schematically shows a perspective sectional view of a part of a drive assembly with schematically indicated movements of elements thereof during setting of a dose.
Figure 3:
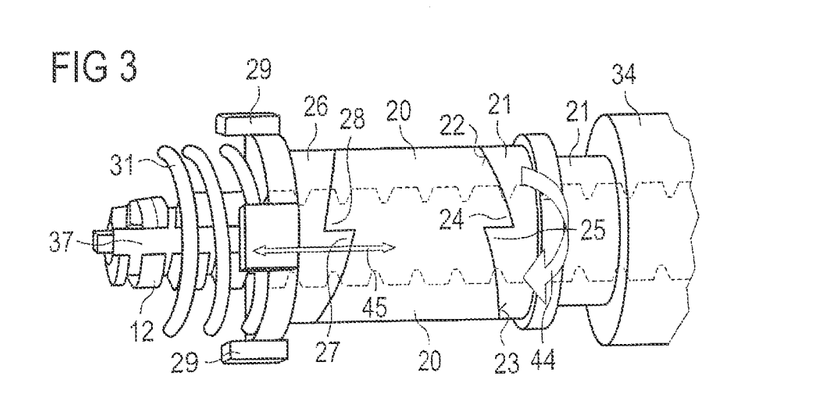
FIG. 3 schematically shows a more detailed side view of a part of FIG. 2.

The drive assembly comprises a housing part 17. The housing part 17 has a proximal end 18 and a distal end 19. The housing part 17 may be (outer) housing 13 of FIG. 1, a part thereof or an insert within housing 13, which insert is preferably secured against rotational and axial movement with respect to housing 13. The housing part 17 may be an insert sleeve, for example. The insert sleeve may be snap-fitted or glued to housing 13, for example. The housing part 17 may have a tubular shape. Housing part 17 may comprise outer fixing elements (not shown), for example snap-fit elements, for fixing housing part 17 to housing 13.

The piston rod 12 is retained in the housing 13, preferably within housing part 17. The piston rod 12 is driven in the distal direction with respect to the housing part 17 during dose delivery.

The drive assembly furthermore comprises a drive member 20. Drive member 20 is retained within the housing part 17. Drive member 20 is configured to transfer force, preferably torque, to the piston rod 12. The transferred force may cause the piston rod 12 to be displaced in the distal direction with respect to the housing part 17 for dose delivery.

Drive member 20 is rotatable with respect to housing part 17. The drive member 20 may engage the piston rod 12. Rotational movement of the drive member 20, for example rotational movement in a second direction may be converted into distal movement of the piston rod 12 with respect to the housing part 17. This is explained in more detail below.

The drive assembly furthermore comprises a rotation member 21. The rotation member 21 is rotatable with respect to the housing part 17 in a first direction, in particular for setting of a dose of the medication, and in a second direction, in particular for delivering the set dose. The second direction is opposite to the first direction. The first direction may be counter-clockwise and the second direction may be clockwise as seen from the proximal end of the device, for example.

Drive member 20, rotation member 21 and/or piston rod 12 are preferably configured to be rotatable about a (common) rotation axis. The rotation axis may extend through drive member 20, rotation member 21 and/or piston rod 12. The rotation axis may be the main longitudinal axis of the piston rod 12. The rotation axis may run between the proximal end and the distal end of the housing part 17.

The rotation member 21 is coupled to the drive member 20 by a uni-directional clutch mechanism, in particular a friction clutch mechanism. This clutch mechanism permits rotational movement of the rotation member 21 with respect to the drive member 20 when the rotation member 21 rotates in the first direction with respect to the housing part 17. The clutch mechanism prevents rotational movement of the rotation member 21 with respect to the drive member 20, when the rotation member 21 rotates in the second direction with respect to the housing part 17. The drive member 20 may thus follow rotational movement of the rotation member 21 in the second direction with respect to the housing part 17.

The drive member 20 is arranged to abut and/or engage the rotation member 21 and, in particular, engages rotation member 21. The drive member 20 comprises a toothing 22 at one end, e.g. its proximal end. The rotation member 21 comprises a toothing 23 at one end which end faces the drive member 20, e.g. its distal end. Toothing 22 comprises a plurality of teeth 24. Toothing 23 comprises a plurality of teeth 25. Teeth 24 and/or 25 may extend along the rotation axis. Toothings 22 and 23 may be configured to mate with one another.

The teeth 24 may be circumferentially disposed on the drive member 20, particularly at the end of the drive member 20 which faces the rotation member 21. The teeth 25 may be circumferentially disposed on the rotation member 21, particularly at the end of the rotation member 21 which faces the drive member 20.

When the steep end faces of two teeth abut and the rotation member 21 is rotated further on in the second direction, the steep sides stay in abutment and drive member 20 follows the rotation of rotation member 21. When the rotation member 21 rotates in the first direction, the ramp of the teeth—which ramps, in particular, run obliquely with respect to the rotation axis—slide along each other and, in consequence, the rotation member 21 may rotate with respect to the drive member 20.

The drive assembly 3 furthermore comprises a stop member 26. The drive member 20 may be arranged between the stop member 26 and the rotation member 21. The stop member 26 is configured for preventing rotational movement of the drive member 20 in the first direction with respect to the housing part 17 during setting of a dose, i.e. when the rotation member 21 rotates in the first direction. Thus, the rotation member 21 may rotate in the first direction with respect to the housing part 17, whereas the drive member 20 and the stop member 26 do not rotate.

The stop member 26 is coupled to the drive member 20 by another uni-directional clutch mechanism, in particular a friction clutch mechanism. This clutch mechanism prevents rotational movement of the drive member 20 with respect to the stop member 26 when the rotation member 21 rotates in the first direction with respect to the housing part 17. The clutch mechanism permits rotational movement of the drive member 20 with respect to the stop member 26, when the rotation member 21 rotates in the second direction with respect to the housing part 17.

Thus, the rotation member 21 may rotate with respect to the drive member 20 and the stop member 26 in the first direction during setting of the dose, with rotation of the drive member 20 being prevented by its interaction with the stop member 26, and rotation member 21 as well as drive member 20 may rotate with respect to the stop member 26 in the second direction during delivery of the dose.

The stop member 26 may be arranged to abut and/or engage the drive member 20 during setting of the dose and, preferably, during delivery of the dose. The stop member 26 has a toothing 27 at one end which faces the drive member 20, e.g. its proximal end. The teeth may be ramp-shaped with a steep side and a less steep ramp. The teeth may be azimuthally disposed along the stop member 26, in particular on the perimeter of the stop member 26.

Drive member 20 has a toothing 28 at one end which faces the stop member 26, e.g. its distal end. Toothings 22 and 28 of the drive member 20 are oppositely disposed. Toothing 28 may be configured in accordance with toothing 21 of the rotation member 21. Toothing 22 may be configured in accordance with toothing 27 of the stop member 26. Toothings 27 and 28, in particular the steep sides of the teeth, do cooperate, e.g. abut, for preventing rotation of the drive member 20 with respect to the housing part 17 and, in particular, with respect to the stop member 26 in the first direction.

Stop member 26 is preferably secured against rotational movement with respect to the housing part 17. Stop member 26 may be fixed to the housing or integrated into the housing. Stop member 26 may be fixed against displacement with respect to the housing part 17 or displacement with respect to the housing part 17 may be allowed.

As it is illustrated in the present embodiment, stop member 26 is displaceable with respect to the housing but non-rotatable with respect to the housing part 17. For that purpose, one or a plurality of, preferably oppositely disposed, guide features, for example guide lugs 29, are provided in the stop member 26. The respective guide feature 29 engages a corresponding guide slot 30 which may be provided in the housing, e.g. in housing part 17. This can be seen in FIGS. 2 and 3. A guide feature 29 cooperates with a guide slot 30 to prevent rotational movement of the stop member 26 with respect to the housing part 17, with axial movement of the stop member 26 with respect to the housing being allowed. The axial movement of the stop member 26 may compensate for play between components of the drive assembly 3 during operation.

From the group comprising drive member 20, stop member 26 and rotation member 21 one or more members, preferably two members or three members, may be axially displaceable (double arrow 45 in FIGS. 2 and 3) with respect to the housing part 17 and, preferably, with respect to the piston rod 12. Therein, the drive member 20 and another one of the recited members may be axially displaceable with respect to the housing. The remaining member may be secured against axial displacement or may also be axially displaceable during operation of the drive assembly 3 for medication delivery. Accordingly, if the drive member 20 and the stop member 26 are axially displaceable, the rotation member 21 may be axially secured or axially displaceable and so on. Play between the components caused by relative (axial) movement of components of the clutch mechanism with respect to the housing can be compensated for in this way. The distance by which the respective components may be axially displaced with respect to the housing may correspond to the (maximum) depth of a tooth of the respective toothing 22 or 28 of the drive member 20. Alternatively, the distance may be greater than the (maximum) depth of a tooth of the respective toothing.

Furthermore, the drive assembly 3 comprises a resilient member 31, preferably a spring member. The resilient member 31 may be biased during medication delivery operation of the drive assembly 3. The resilient member 31 may provide for a force that tends to keep the drive member 20 in engagement with the stop member 26 and/or the rotation member 21. The force may be exerted along the rotation axis. In the situation shown in the FIGS. 2 and 3, this force may be exerted in the proximal direction. The resilient member 31 may be a helical (coil) spring. The resilient member 31 may be a compression spring.

The resilient member 31 may keep the drive member 20 and the stop member 26 in (permanent) mechanical contact, e.g. in abutment, with each other during setting and delivery of a dose of the medication. Alternatively or additionally, the resilient member 31 may keep the drive member 20 and the rotation member 21 in (permanent) mechanical contact, preferably abutment, with each other during setting and delivery of a dose of the medication.

The resilient member 31 may be integrated within stop member 26 or a separate component. The resilient member 31 may be arranged on the distal end side of the stop member 26.

The drive assembly 3 furthermore comprises a support member 32. Support member 32 is expediently fixed against axial and rotational movement with respect to the housing part 17 or integrated into housing part 17. Support member 32 is arranged on that side of the drive member 20 which is remote from the stop member 26. Support member 32 may be a protrusion, for example a ring-like protrusion. Rotation member 21 may extend through an opening in support member 32. The support member 32 may provide for a counter force to the force which is exerted by the resilient member 31. Permanent abutment of the rotation member 21 with the drive member 20 and of the drive member 20 with the stop member 26 during setting and delivery of medication is facilitated in this way.

The rotation member 21 has an (radially) outwardly protruding member 33, for example a flange portion. The protruding member 33 is expediently provided for abutting support member 32, in particular the distal end side of support member 32.

The drive assembly 3 furthermore comprises a dose member 34. Dose member 34 may be dose part 16 or may be a part of the dose part 16 of FIG. 1. Dose member 34 is movable with respect to the housing in the proximal direction (arrow 43) for setting of a dose and for delivery of the dose. For example, the dose member 34 may be moved in the proximal direction with respect to the housing part 17 during dose setting and in the distal direction with respect to the housing part 17 during dose delivery. The dose member 34 may engage the housing part 17 or, alternatively, another part of housing 13 (not explicitly shown). Dose member 34 is preferably secured against rotational movement with respect to the housing part 17. The dose member 34 may comprise a guide feature 35, for example a guide lug or a guide slot, that engages another guide feature, for example a guide slot or a guide lug, respectively, that is provided in the housing part 17 or the housing 13.

Dose member 34 may be moved in the proximal direction and in the distal direction with respect to rotation member 21. Dose member 34 is arranged to be coupleable and is preferably (permanently) coupled to rotation member 21 such that movement of the dose member, e.g. in the proximal direction with respect to the housing part 17, for setting a dose of the medication is converted into rotational movement of the rotation member 21 in the first direction (arrow 44) and movement of the dose member, e.g. in the distal direction with respect to the housing part 17, for delivering the dose is converted into rotational movement of the rotation member 21 in the second direction opposite to the first direction.

The rotation member 21 may be provided with an (outer) thread 36. Thread 36 may be engaged with one of or a plurality of engagement members 49 of dose member 34. The respective engagement member may be arranged on the inside of the dose member. The respective engagement member may be a thread or a part of a thread, for example. Thus, dose member 34 and rotation member 21 may be threadedly coupled, in particularly threadedly engaged. The rotation member 21 may be arranged inside the dose member 34.

The drive member 20 and the piston rod 12 are configured for rotational movement of the drive member 20 with respect to the housing being converted into rotational movement of the piston rod 12 with respect to the housing. The drive member 20 may engage the piston rod 12. The piston rod 12 is displaceable with respect to the drive member 20 along a displacement axis. Presently, the displacement axis runs along the rotation axis. The drive member 20 may be splined to the piston rod 12, for example.

The piston rod 12 may be threadedly coupled to the housing 13. The piston rod 12 may be provided with an outer thread, for example. The piston rod 12 comprises an engagement track 37, preferably two oppositely disposed engagement tracks 37, on the outside. The (respective) engagement track 37 may interrupt the outer thread of the piston rod 12. The (respective) engagement track 37 preferably extends along the axis along which the piston rod 12 is displaceable with respect to the housing and, in particular, with respect to the drive member 20.

Rotational movement of the drive member 20 with respect to the housing may thus be converted into rotational movement of the piston rod 12 with respect to the housing and the rotational movement of the piston rod 12 is, on account of the threaded engagement of the piston rod 12 and the housing (part), converted into movement of the piston rod 12 with respect to the housing in the distal direction.

The dose part 16 (cf. FIG. 1) may comprise a dose button 48. Dose button 48 may be configured to be gripped by a user. Dose button 48 may be arranged and connected to the dose member 34 at the proximal end. Dose button 48 and dose member 34 may be unitary.

Figure 4A:
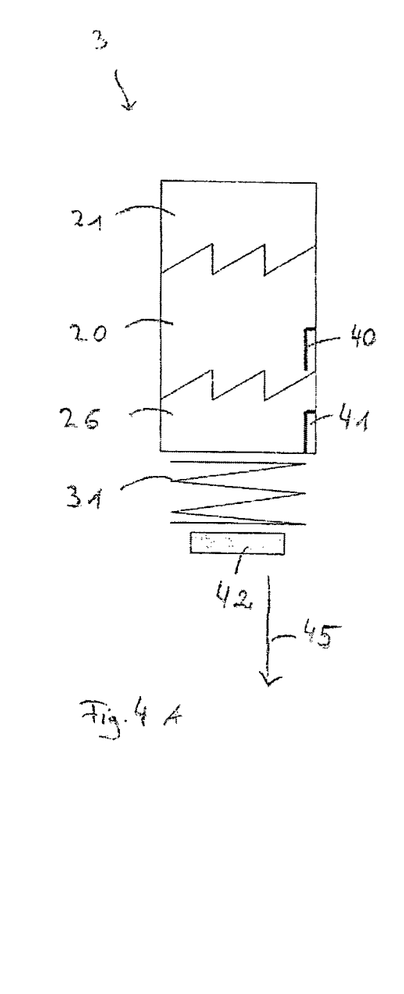
FIG. 4A schematically shows the concept of a drive assembly in the operational state, suitable for gravity separation for switching into the resetting state.

Turning now to FIG. 4A the basic principle of a drive assembly 3 separable under gravity for switching into a resetting state is described. FIG. 4A shows the three elements of the drive assembly, i.e. the rotation member 21, the drive member 20 as well as the stop member 26. The functional engagement of the three elements in the operational state has been explained above with respect to FIGS. 2 and 3. Furthermore, a resilient member 31 according to the FIGS. 2 and 3 is depicted. In the operational state according to FIG. 4A, the resilient member 31 is strained due to a medication receptacle (not shown) which may be inserted into or attached to a housing (see housing 13 of FIG. 1) of the drive assembly 3. The strained state of the resilient member 31 is here schematically illustrated. The resilient member 31 provides a force for keeping the stop member 26, the drive member 20 and the rotation member 21 in engagement, thereby holding the stop member 26 and the drive member 20 in respective first positions. Furthermore, a spring cap 42 is provided which acts as coupling means between the medication receptacle and the resilient member 31. The drive member 20 and the stop member 26 comprise stopping members 40 and 41, the functionality of which is described below.

For switching the drive assembly from the operational state as depicted in FIG. 4A into a resetting state as explained below, the medication receptacle (see medication receptacle 2 of FIG. 1) has to be removed from the housing (see housing 13 of FIG. 1) of the drive assembly 3. The assembly of FIG. 4A can be separated under gravity by bringing the drive assembly into a predetermined position as shown in FIG. 4A with the distal end of the drive assembly pointing downwards, the resilient member 31 and the spring cap 42 located below other members. Thus, gravity force can cause a separation of the assembly. The three elements, i.e. rotation member 21, drive member 20 and stop member 26 can be separated by a movement of the drive member 20 and the stop member 26 in distal direction which is illustrated by the arrow 45.

Figure 4B:
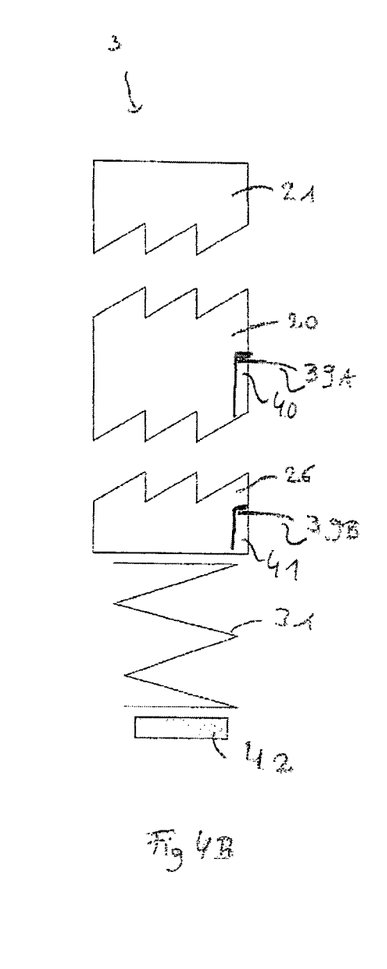
FIG. 4B schematically shows the concept of a drive assembly in the resetting state after gravity separation.

FIG. 4B shows the drive assembly 3 according to FIG. 4A which has now been separated under gravity, i.e. the rotation member 21, drive member 20 and stop member 26 have been disengaged from each other under gravity. As the medication receptacle (not shown) has been removed from a housing of the drive assembly 3, the resilient member 31 is unstrained with the spring cap 42 being placed in a downward final position. Preferably, the spring cap 42 can be held in its final position by stopping means (not shown). As the resilient member 31 is unstrained in this state thereby not providing a force on the three members, the three elements 20, 21 and 26 have become disengaged, whereby the drive member 20 has slid downwards and disengaged from the rotation member 21 and the stop member 26 has slid downwards and disengaged from the drive member 20. Thereby, the traverse path of the stop member 26 is longer than the traverse path of the drive member 20 such that all of the three elements 20, 21 and 26 are fully separated. As schematically illustrated in FIG. 4B the drive member 20 abuts with its stopping member 40 at first mechanical stopping means 39A of the housing and the stop member 26 abuts with its stopping member 41 at second mechanical stopping means 39B of the housing. This is suitable for holding the drive member 20 and the stop member 26 in respective second positions after gravity separation has been accomplished such that the drive member 20 and the stop member 26 are undetachably connected to the housing of the drive assembly 3.

By bringing the drive assembly 3 in the predetermined position as depicted in FIGS. 4A and 4B and by removing a medication receptacle from the drive assembly 3, the drive assembly 3 is switchable from an operational state into a resetting state, wherein the three elements 20, 21 and 26 of the drive assembly 3 can be separated under gravity due to the weight of the drive member 20 and the weight of the stop member 26 which are sliding downwards under gravity, the drive member 20 disengaging from the rotation member 21 and the stop member 26 disengaging from the drive member 20.

Figure 5A:
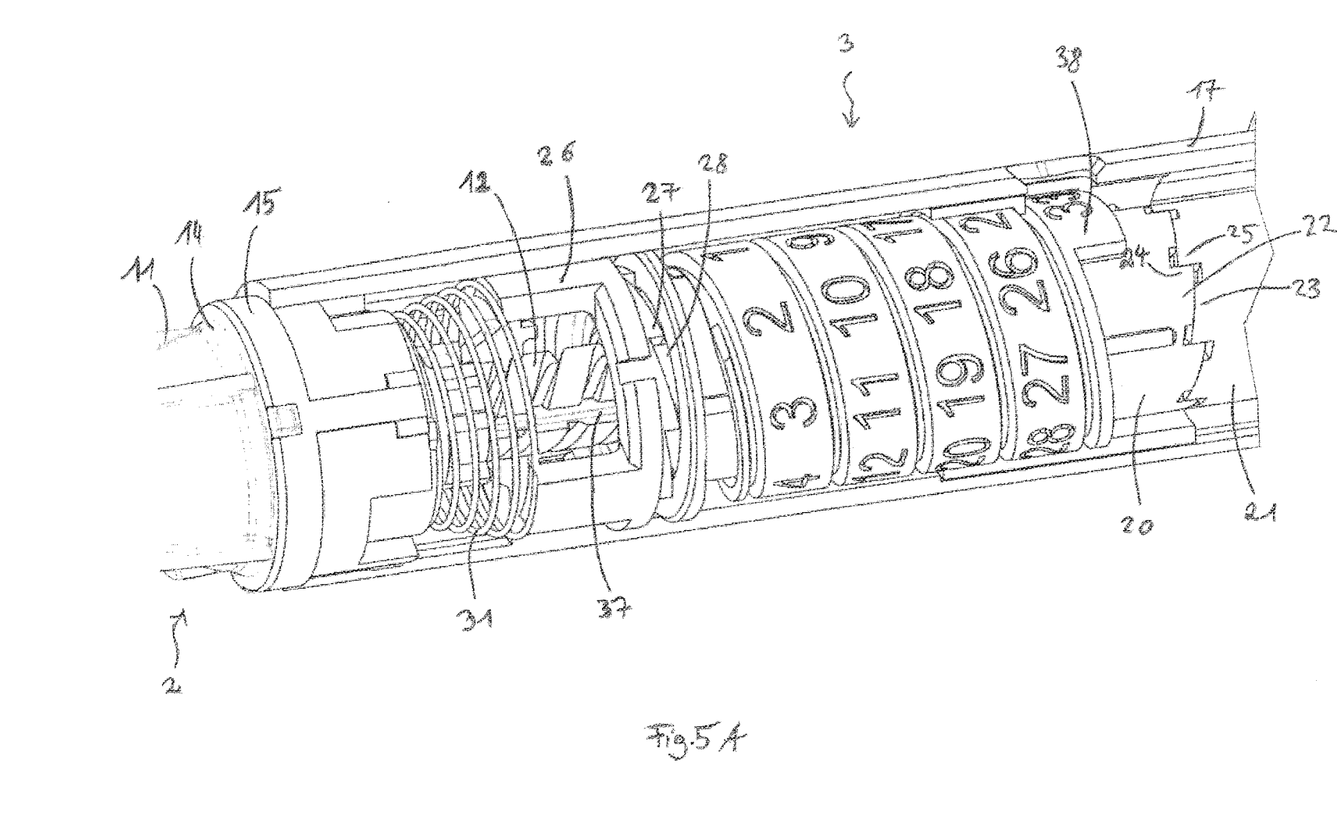
FIG. 5A schematically shows a perspective partly sectional side view of an exemplary embodiment of a medication delivery device in the operational state.

FIG. 5A schematically shows a partly sectional view of a part of a medication delivery device. According to the embodiment, the device is a fixed dose reusable device. The drive assembly 3 is in the operational state comprising the separable drive assembly of FIGS. 4A and 4B. FIG. 5A shows a medication receptacle 2 with a cartridge retaining member 11 which is inserted with its proximal end side 14 in the distal end side 15 of the housing part 17 of the drive assembly 3. As a result, the resilient member 31 is strained because of the proximal end side 14 of the cartridge retaining member 11 pushing the resilient member 31 against the distal end side of the stop member 26. Hence, the resilient member 31 provides a force for engagement of stop member 26 with drive member 20 as well as for engagement of drive member 20 with rotation member 21. This results in engagement of the toothing 27 of the stop member 26 and the toothing 28 of the drive member 20 as well as the toothing 22 of the drive member 20 and the toothing 23 of the rotation member 21 at their respective teeth 24 and 25 as already explained above.

Besides, the drive assembly 3 of the embodiment of FIG. 5A comprises a number sleeve 38 which may indicate and show e.g. the number of doses of a medication remaining in the cartridge. For delivering a dose of a medication the drive assembly 3 further comprises a piston rod 12. The piston rod 12 is held in engagement with the drive member 20 via an engagement track 37 which is longitudinally arranged at the piston rod 12 such that rotational movement of the drive member 20 is converted into movement of the piston rod 12. Thus, the drive member 20 drives the piston rod 12 in distal direction with respect to the part of the housing 17 during delivery of the dose as described above. Thereby, rotational movement of the drive member 20 preferably is converted into helical movement of the piston rod 12 via a conversion element, in particular a nut means or body nut.

Figure 5B:
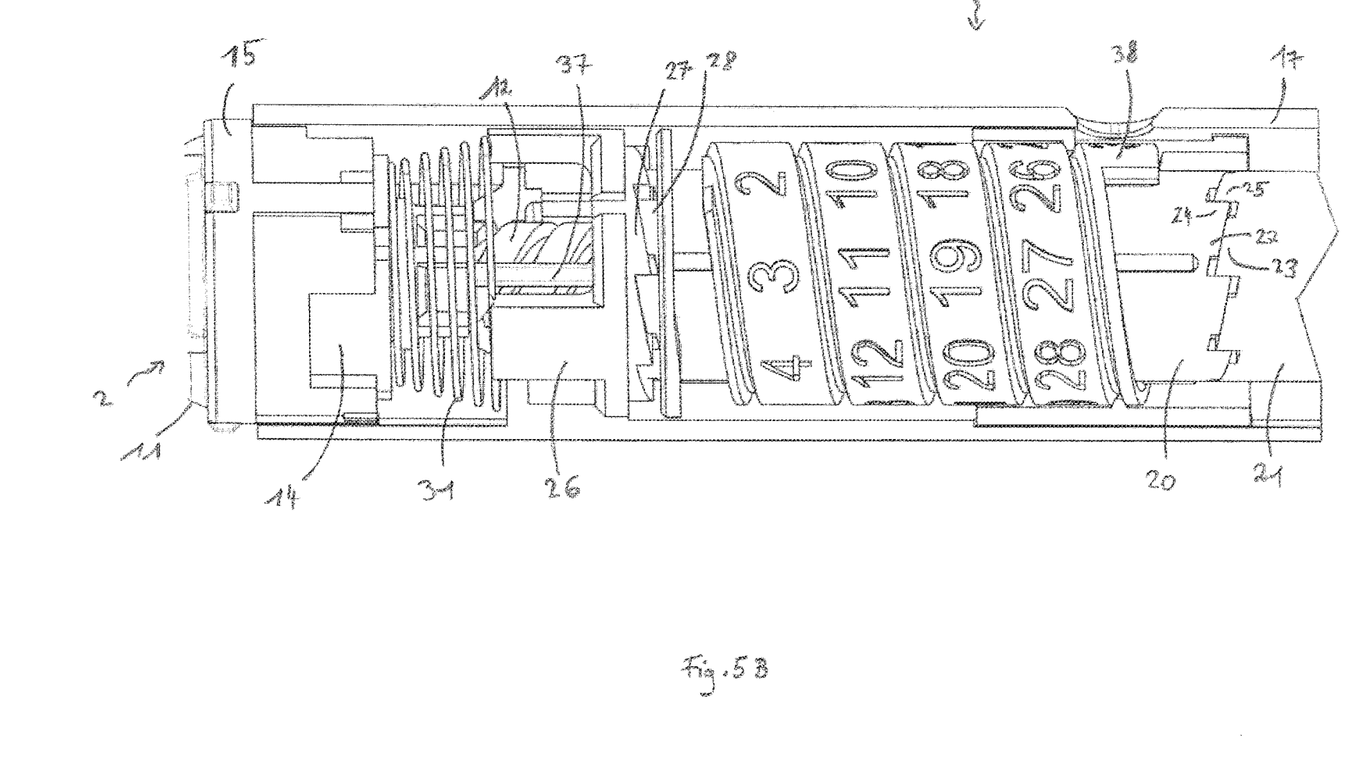
FIG. 5B shows a partly sectional side view of the embodiment of FIG. 5A.

FIG. 5B shows a partly sectional side view of the embodiment of FIG. 5A. FIG. 5B illustrates the arrangement of the resilient member 31 between the proximal end side 14 of the cartridge retaining member 11 and the stop member 26 of the drive assembly 3. A spring cap 42 according to FIGS. 4A and 4B may be located between the proximal end side 14 of the cartridge retaining member 11 and the resilient member 31 to align and retain the resilient member 31 in the assembly and enable a suitable contact between the resilient member and the cartridge retaining member to guarantee contact against the cartridge retaining member 11 as required. As the drive assembly 3 is in the operational state, the resilient member 31 is strained by the proximal end side 14 of the cartridge retaining member 11 which is inserted in the housing part 17. Hence, the proximal end side 14 of the cartridge retaining member 11 comes in contact with the distal end of the resilient member 31 and presses the resilient member 31 with its proximal end against the stop member 26, whereby the resilient member 31 becomes strained.

Accordingly, the resilient member 31 establishes a force for pressing the stop member 26 against the drive member 20 and the drive member 20 against the rotation member 21. With the cartridge retaining member 11 inserted into the distal end side 15 of the housing part 17, the resilient member 31 holds the elements 26, 20 and 21 of the drive assembly 3 in engagement with each other, i.e. the stop member 26 is held in a respective first axial position and the drive member 20 is held in a respective first axial position according to this operational state.

According to the embodiment of FIG. 5B the resilient member 31 is arranged at the distal end side 15 of the housing part 17, wherein the stop member 26 and drive member 20 are pressed in proximal direction towards and against the rotation member 21 which, in this embodiment, is secured against axial movement with respect to the housing part 17.

Figure 6A:
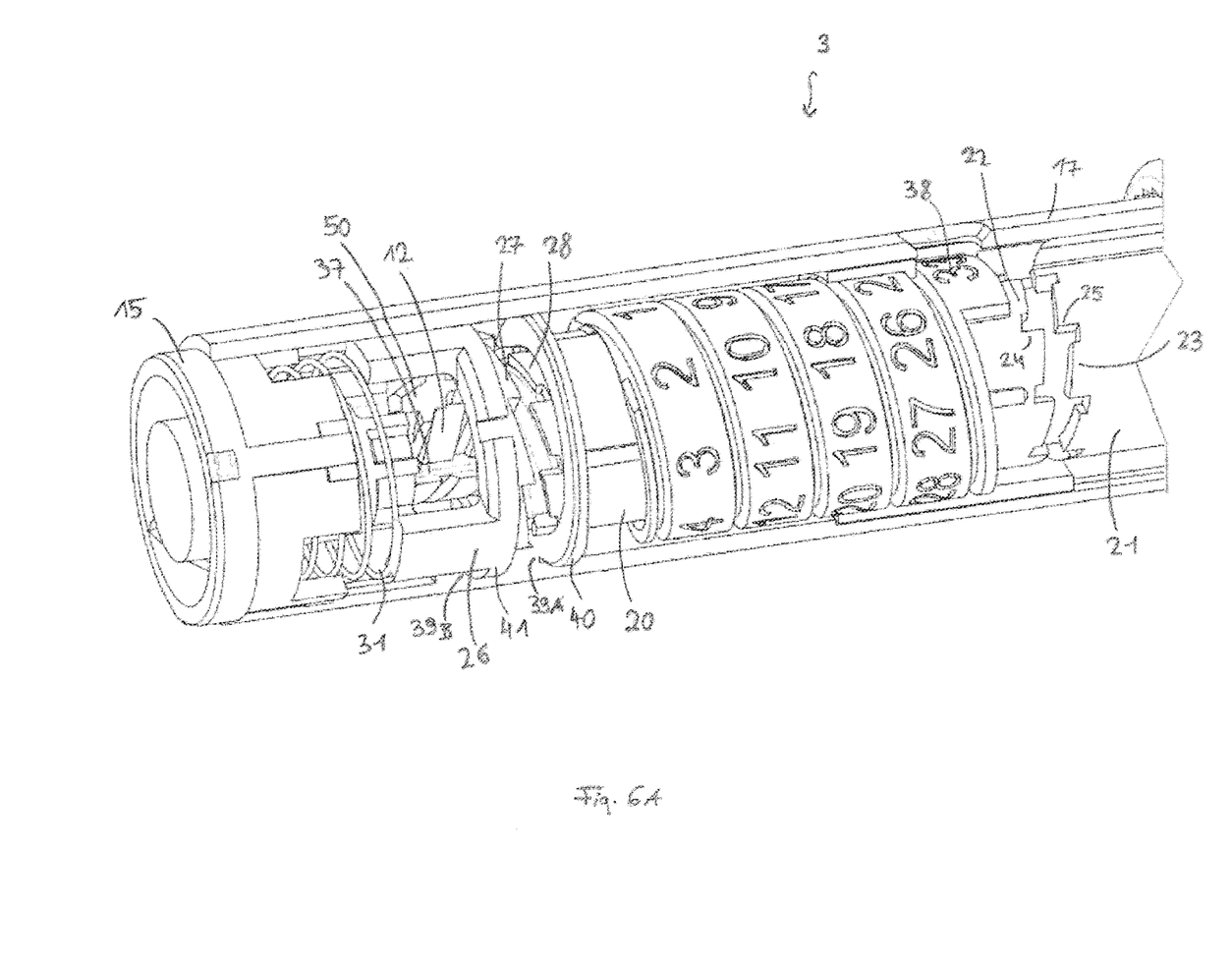
FIG. 6A schematically shows a perspective partly sectional view of the embodiment of the FIGS. 5A and 5B in the resetting state.

FIG. 6A shows a partly sectional perspective view of the embodiment of FIGS. 5A and 5B, wherein the device now is in the resetting state. The medication receptacle 2 (see FIGS. 5A and 5B) has been removed from the distal end side 15 of the housing part 17 of the drive assembly 3. As a result, the resilient member 31 has become unstrained and slid in distal direction towards the distal end side 15 of the housing part 17. Although not explicitly shown in FIG. 6A, the drive assembly 3 has been brought into the predetermined position with the distal end side 15 pointing downwards as explained with respect to FIGS. 4A and 4B. There, the resilient member is held, e.g. by a spring cap (see FIGS. 4A and 4B), which itself interacts with an abutment on the housing or a component fixed to the housing part 17 such that the resilient member 31 is undetachably connected to the housing part 17.

Due to the unstrained state of the resilient member 31 and its downward sliding, the distal end side 15 of the housing part 17, the stop member 26 as well as the drive member 20 can also be axially moved in distal direction with respect to the housing part 17 as they are no longer held in engagement by the resilient member 31. Hence, by bringing the drive assembly 3 in the predetermined position (see FIGS. 4A and 4B) with the distal end side 15 of the housing part 17 pointing downwards, the three elements 26, 20 and 21 of the drive assembly 3 can be separated, caused by gravity, wherein the stop member 26 slides downwards in a second position due to its own weight, thereby disengaging from the drive member 20 and wherein the drive member 20 slides downwards in a respective second position, thereby disengaging from the rotation member 21. It follows that all members of the drive assembly 3 have become disengaged from each other in the resetting state as depicted in FIG. 6A.

In the resetting state of the drive assembly, the piston rod 12 is movable in the proximal direction, e.g. manually movably by exerting a force on the distal end of the piston rod, movable by a cartridge retaining member being attached to the housing or movable by a new or full cartridge of medicament being installed into the cartridge retaining member.

As the drive member 20 and the piston rod 12 are engaged with each other, movement of the piston rod 12 in proximal direction is converted into rotational movement of the drive member 20 in the first direction that is opposite to the second direction for driving the piston rod 12 in distal direction during medication delivery (see FIGS. 2 and 3). The piston rod 12 is urged into helical movement by a conversion element 50, for example a nut means or body nut, through which the piston rod 12 passes and which may be threadedly engaged with the piston rod 12 such that the piston rod 12 during axial movement at least partially is rotationally moved. A resetting of the piston rod 12 according to this concept may be only enabled during the resetting state with the elements 26, 20 and 21 of the drive assembly 3 being separated from each other under gravity. In the resetting state the drive member 20 is allowed to freely rotate with the piston rod 12 in a first direction with respect to the housing part 17 such that the piston rod 12 can be pushed back in proximal direction with respect to the housing part 17.

Figure 6B:
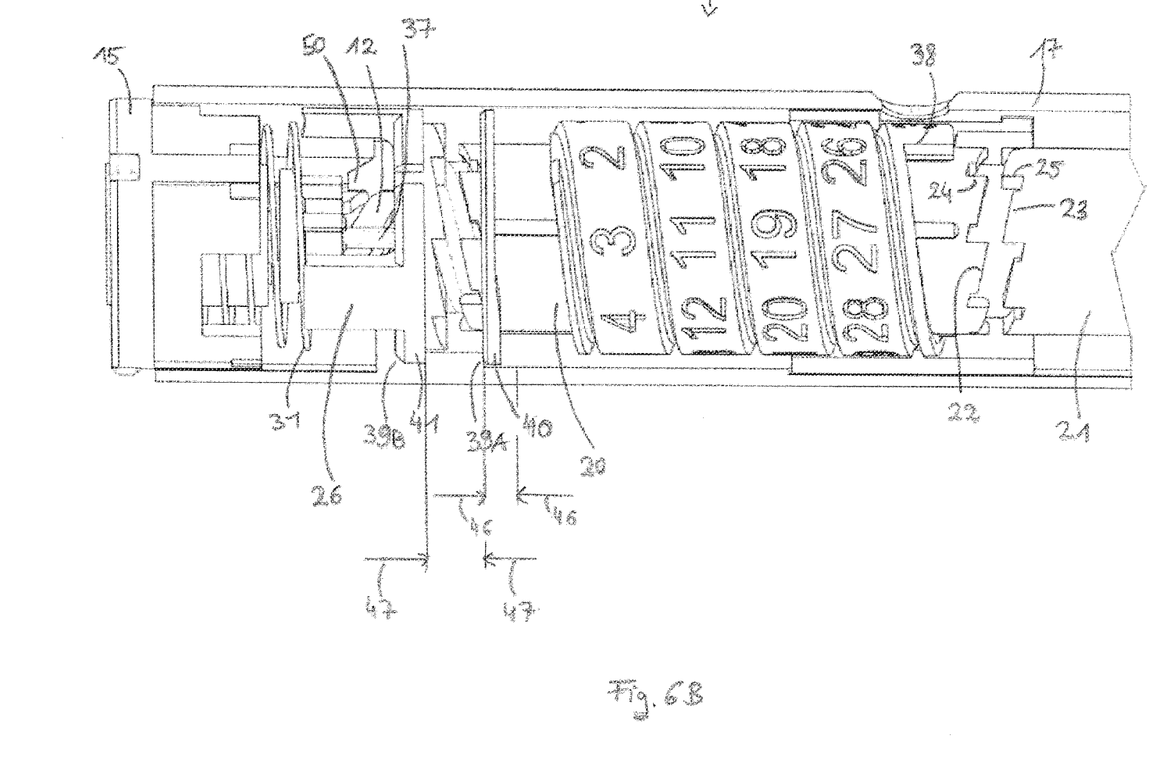
FIG. 6B schematically shows a partly sectional side view of the embodiment of FIG. 6A.

FIG. 6B shows a partly sectional side view of the embodiment of FIG. 6A in the resetting state. FIG. 6B illustrates the resilient member 31 which has slid in distal direction with respect to the housing part 17 towards the distal end side 15 of the housing part 17 due to the fact that a medication receptacle 2 has been removed from the distal end side 15 and the drive assembly 3 has been brought into the predetermined position for gravity separation as explained above. Furthermore, FIG. 6B illustrates the respective second axial positions of the stop member 26 and the drive member 20, wherein the stop member 26 has been separated from the drive member 20 and wherein the drive member 20 has been separated from the rotation member 21 caused by gravity.

The stop member 26 abuts with its stopping member 41 at mechanical stopping means 39B which is formed by protrusions on the inner diameter of the housing part 17. The drive member 20 abuts with its stopping member 40 at respective mechanical stopping means 39A which is also formed by a protrusion formed on the inner diameter of the housing part 17. The respective traverse paths of the stop member 26 and the drive member 20 are illustrated by arrows 47 and 46 marking the distances between the respective first and second positions of stop member 26 and drive member 20. In particular, the arrows 46 mark the traverse path of the drive member 20 and the arrows 47 mark the traverse path of the stop member 26. Preferably the traverse path of the stop member 26 is longer than the traverse path of the drive member 20 such that after gravity separation an interspace between rotation member 21 and drive member 20 as well as an interspace between the drive member 20 and the stop member 26 can be obtained. As an example, the traverse path of the stop member 26 is twice the traverse path of the drive member 20 such that the interspaces between rotation member 21 and drive member 20 as well as drive member 20 and stop member 26 are equidistant.

In all of the embodiments explained above the stop member 26 is preferably secured to the housing 13 or 17 against rotational movement such that the stop member 26 can inhibit rotational movement of the drive member 20 in the first direction with respect to the housing 13 or 17 in the operational state. Beyond, it is conceivable that in further embodiments which are not shown, the resilient member 31 can be positioned at a proximal end side of the housing 13 or 17 of the drive assembly 3, whereby a proximal end side 14 of a cartridge retaining member 11 interacts with the stop member 26 for pressing it against the drive member 20 and for pressing the drive member 20 against the rotation member 21 such that all of the three members 26, 20 and 21 are pressed in proximal direction against the resilient member 31 when the medication receptacle 2 is inserted into the housing 13 or 17 of the drive assembly 3.

The embodiments shown in the figures and explained above are only exemplary and do not restrict the invention.

The invention claimed is:

1. A drive assembly for a medication delivery device being switchable from an operational state to a resetting state and comprising:
   a housing having a proximal end and a distal end,
   a drive member adapted to be rotated with respect to the housing,
   a stop member adapted to prevent rotational movement of the drive member in a first direction with respect to the housing in the operational state and to permit rotational movement of the drive member in a second direction with respect to the housing in the operational state, the second direction being opposite to the first direction,
   a resilient member adapted to provide a force for engagement of the stop member and the drive member in the operational state,
   wherein in the operational state of the drive assembly the stop member is held in engagement with the drive member, and
   for switching into the resetting state of the drive assembly the stop member is enabled to disengage from the drive member caused by gravity due to the weight of the stop member.

2. The drive assembly according to claim 1, comprising a rotation member adapted to be rotated in the first direction with respect to the housing during setting of a dose of a medication and to be rotated in the second direction with respect to the housing during delivery of the dose.

3. The drive assembly according to claim 2, wherein the rotation member is arranged at an opposite side of the drive member with respect to the stop member.

4. The drive assembly according to claim 2, wherein in the operational state of the drive assembly the drive member is held in engagement with the rotation member, and for switching into the resetting state of the drive assembly the drive member is enabled to disengage from the rotation member caused by gravity due to the weight of the drive member.

5. The drive assembly according to claim 2, wherein the resilient member is adapted to provide a force for engagement of the drive member and the rotation member in the operational state.

6. The drive assembly according to claim 1, wherein the resilient member is adapted to interact with a medication receptacle of a medication delivery device such that when the respective medication receptacle is engaged with the housing the resilient member is strained, thereby providing the force, and when the respective medication receptacle is disengaged from the housing the resilient member is unstrained, thereby not providing the force.

7. The drive assembly according to claim 2, wherein in the operational state the drive member is adapted to follow rotational movement of the rotation member in the second direction with respect to the housing during delivery of the dose.

8. The drive assembly according to claim 7, wherein in the operational state the drive member and the rotation member are coupled to one another by a first uni-directional friction clutch mechanism, which is configured to permit relative rotational movement between rotation member and drive member during rotation of the rotation member in the first direction for setting of the dose and to prevent relative rotational movement of rotation member and drive member during rotation of the rotation member in the second direction for delivery of the dose.

9. The drive assembly according to claim 8, wherein in the operational state the stop member and the drive member are coupled to one another by a second uni-directional friction clutch mechanism, which is configured to prevent relative rotational movement between stop member and drive member in the first direction with respect to the housing and to permit relative rotational movement of stop member and drive member in the second direction with respect to the housing.

10. The drive assembly according to claim 1, wherein in the resetting state the stop member or both the stop member and the drive member are adapted to be movable in the distal direction with respect to the housing caused by gravity, the traverse path of the respective members in distal direction with respect to the housing being delimited by mechanical stopping means.

11. The drive assembly according to claim 10, wherein the traverse path of the stop member is longer than the traverse path of the drive member.

12. The drive assembly according to claim 1, comprising a piston rod adapted to be displaced in the distal direction with respect to the housing for delivering a dose of a medication, wherein in the operational state of the drive assembly rotational movement of the drive member in the second direction with respect to the housing is converted into movement of the piston rod in the distal direction with respect to the housing, and in the resetting state of the drive assembly rotational movement of the piston rod in the proximal direction with respect to the housing is converted into rotational movement of the drive member in the first direction with respect to the housing.

13. A medication delivery device comprising the drive assembly according to claim 1 and a medication receptacle, the medication receptacle being removable from a housing of the drive assembly and being configured for containing at least one dose of a medication.

14. The medication delivery device according to claim 13, wherein the drive assembly comprises the drive member and a piston rod, the drive member cooperating with the piston rod for displacing the piston rod in a distal direction with respect to the housing of the drive assembly for delivering a dose of a medication, and wherein the device is switchable from an operational state into a resetting state by removing the medication receptacle from the housing of the drive assembly, and wherein in the resetting state the piston rod is movable in a proximal direction into the housing of the drive assembly by bringing the device into a predetermined position.

15. The medication delivery device according to claim 14, wherein the predetermined position is a vertical position of the device with the piston rod pointing downwards.

16. The drive assembly according to claim 1, wherein in the resetting state of the drive assembly the stop member and the drive member are disengaged such that the drive assembly becomes resettable and a resetting movement of the drive member in the first direction can be performed.

17. The drive assembly according to claim 1, wherein the stop member is rotationally fixed in the housing.

18. The drive assembly according to claim 2, further comprising a piston rod configured to be displaced in the distal direction with respect to the housing for delivering a dose of a medication responsive to the drive member rotating in the second direction, wherein the piston rod is distinct from the rotational member.

19. The drive assembly according to claim 1, wherein a disengagement of the stop member from the drive member is realized under gravity such that no further elements are necessary for separating the stop member from the drive member.

20. A drive assembly for a medication delivery device being switchable from an operational state to a resetting state and comprising:

a housing having a proximal end and a distal end, a drive member adapted to be rotated with respect to the housing, and a stop member adapted to prevent rotational movement of the drive member in a first direction with respect to the housing in the operational state and to permit rotational movement of the drive member in a second direction with respect to the housing in the operational state, the second direction being opposite to the first direction, wherein in the operational state of the drive assembly the stop member is held in engagement with the drive member, and for switching into the resetting state of the drive assembly the stop member is enabled to disengage from the drive member caused by gravity due to the weight of the stop member wherein a disengagement of the stop member from the drive member is realized under gravity such that no further elements are necessary for separating the stop member from the drive member.

\* \* \* \* \*